United States Patent [19]

Weissman et al.

[11] Patent Number: 5,569,923
[45] Date of Patent: Oct. 29, 1996

[54] FIBER OPTIC REFLECTANCE PROBE

[75] Inventors: Yitzhak Weissman, Tel-Aviv; Rami Herman; Aharon Bornstein, both of Rishon-LeZion; Israel Tugendhaft, Jerusalem, all of Israel

[73] Assignee: The State of Israel Atomic Energy Commission Soreq Nuclear Research Center, Yavne, Israel

[21] Appl. No.: 404,504

[22] Filed: Mar. 15, 1995

[30] Foreign Application Priority Data

Mar. 31, 1994 [IL] Israel ......................................... 109181

[51] Int. Cl.⁶ ................................................. G01N 21/01
[52] U.S. Cl. ..................................... 250/341.2; 250/339.11
[58] Field of Search ........................... 250/341.2, 338.1, 250/338.5, 339.11, 341.8, 343; 128/633, 664

[56] References Cited

U.S. PATENT DOCUMENTS

| | | |
|---|---|---|
| 4,241,738 | 12/1980 | Lubbers et al. . |
| 4,423,736 | 1/1984 | DeWitt et al. . |
| 4,608,990 | 9/1986 | Elings . |
| 5,185,834 | 2/1993 | Day et al. ................................ 385/47 |
| 5,436,454 | 7/1995 | Bornstein et al. .................. 250/341.2 |

FOREIGN PATENT DOCUMENTS

| | | |
|---|---|---|
| 0047094 | 3/1982 | European Pat. Off. . |
| 0358203 | 3/1990 | European Pat. Off. . |
| 2596530 | 3/1986 | France . |
| 2215984 | 10/1972 | Germany . |

OTHER PUBLICATIONS

"Near–Infrared . . . Pharmaceuticals", Galante et al., Anal. Chem. 1990, vol. 62, No. 23, Dec. 1, 1990, pp. 2514–2521.

*Primary Examiner*—Davis L. Willis
*Assistant Examiner*—Richard Hanig
*Attorney, Agent, or Firm*—Helfgott & Karas, PC.

[57] ABSTRACT

There is disclosed a fiber optic probe for infrared (IR) spectroscopy of a kind which serves both for illuminating a fluid or solid sample and for collecting the light reflected therefrom for spectral analysis. The probe has a tubular sheath with an inner, infrared radiation reflecting surface, holding light input and output optical fibers. The sheath has a sampling tip and the optical fibers stop short of the edge, forming with the sampling tip a sampling cavity.

4 Claims, 1 Drawing Sheet

5,569,923

FIBER OPTIC REFLECTANCE PROBE

FIELD OF THE INVENTION

The present invention relates to a fiber optic probe for infrared (IR) spectroscopy of a kind which serves both for illuminating a fluid or solid sample and for collecting the light reflected therefrom for spectral analysis.

BACKGROUND OF THE INVENTION

Many inorganic and almost all organic chemicals have IR spectra that can be used for identification, characterization and determination of their concentration in mixtures and it has already been proposed to use for the purpose probes of the kind specified.

In its simplest form an IR fiber optic probe for spectral analysis consists of two optical fibers capable of transmitting IR radiation: one, which is attached to a light source, and serves to illuminate a sample, and the other which is attached to a spectrometer serves for collecting and transmitting light arriving from the sample.

For their many applications in the fields of chemistry, biology and others and which may include, among others, in vivo measurement of biochemical occurrences in tissues, fiber optic probes must satisfy a variety of requirements such as good optical characteristics, slenderness, flexibility, and sufficient toughness to enable introduction into an endoscope channel.

EP 0358 203 describes a fiber optic probe for measuring a reflectance spectrum. This probe comprises a light illuminating optical fiber and a light receiving optical fiber coupled in parallel to form a fiber bundle which is inserted in a coating tube, and is also provided with a lens placed at the end portion of the fiber bundle which serves as a condensing means. The probe is rather expensive with relatively low efficiency.

Other types of fiber optic probes for IR spectroscopy include an attenuated total reflection (ATR) element for receiving and transmitting attenuated IR light such as in U.S. Pat. No. 5,170,056 and U.S. Pat. No. 5,185,834. Such probes are, however, relatively complex and their manufacture is complicated and expensive.

Research Disclosure No. 295087 of November 1988 describes a device for illuminating fluid samples and collecting scattered and emitted light therefrom. It comprises a fiber-optic probe having at least one illuminating optical fiber and at least one collecting optical fiber, and in order to increase the collection efficiency, the tested sample is contained within a sample tube having a reflective inner surface. The probe and sample tube are separate parts and accordingly in operation they have to be carefully aligned, the accuracy of the measurement being contingent on the accuracy of alignment, which is an obvious disadvantage. A further, fundamental disadvantage of this device is that it is suitable only for sampling liquid materials and is inapplicable for solid ones.

It is the object of the present invention to provide an improved fiber optic probe for IR spectroscopy, free of the above disadvantages and suitable for use on both fluid and solid samples.

SUMMARY OF THE INVENTION

In the following the term "reflectance probe" will be used for a probe designed to collect radiation in response to illumination regardless of whether the collected light is scattered, reflected or emitted.

In accordance with the present invention there is provided a fiber optic reflectance probe for infrared spectroscopy of a sample, comprising a tubular sheath opaque to infrared radiation and having a tubular sampling tip with a terminal edge and an infrared radiation reflecting coating, which tubular sheath holds at least one light input optical fiber and at least one light output optical fiber which input and output optical fibers terminate within said tubular sampling tip short of the terminal edge thereof so as to form with the latter a sampling cavity.

In accordance with one embodiment of the invention the tubular sampling tip is formed within an end portion of the tubular sheath. In accordance with another embodiment, the tubular sampling tip is a detachable tubular sleeve mounted on one end of the sheath.

In accordance with a preferred embodiment of the invention the inner wall of the sampling cavity has a gold coat whereby a high IR reflectivity is attained.

It has been found that the fiber optic reflectance probe according to the invention is most effective in mid-infrared spectroscopy and can be used effectively for analyzing opaque and optically diffused fluid and solid samples. One of the most distinctive and advantageous features of the probe according to the invention is its ability to analyze solid samples regardless of their surface finish, i.e. of whether they are polished or rough. Accordingly, for IR analysis with the aid of a probe according to the invention, it is sufficient to simply establish physical contact between the sampling cavity and the sample and there is no need for sample preparation.

A further attractive feature of the probe according to the invention is its small dimensions which enable sampling in hard-to-reach locations and also provides good spatial resolution of the order of 1 mm.

Preferably, the IR transmitting optical fibers in a fiber optic reflectance probe according to the invention are made of chalcogenide glass, alternative materials being fluoride glass and polycrystalline silver halide glass.

DESCRIPTION OF THE DRAWINGS

For better understanding the invention will now be described, by way of example only, with reference to the annexed drawings in which.

DETAILED DESCRIPTION OF PREFERRED EMBODIMENTS

Figure 1:
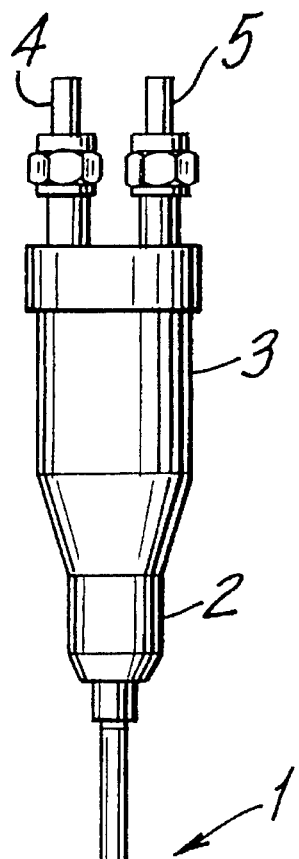
FIG. 1 is an elevation of a fiber optic reflectance probe according to the invention.
Figure 2:
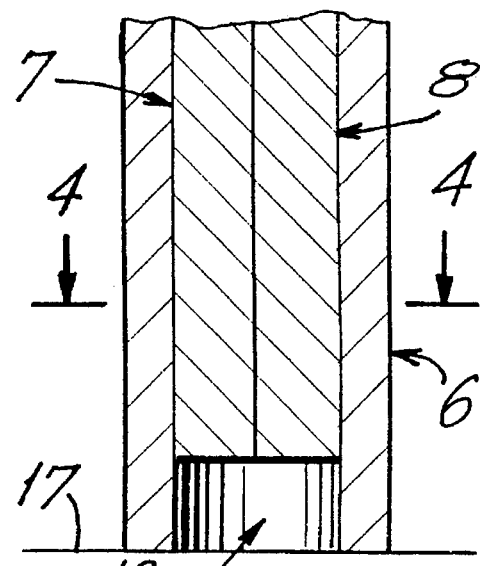
FIG. 2 is a cutaway view of an end portion of the probe of FIG. 1, drawn to a larger scale.
Figure 4:
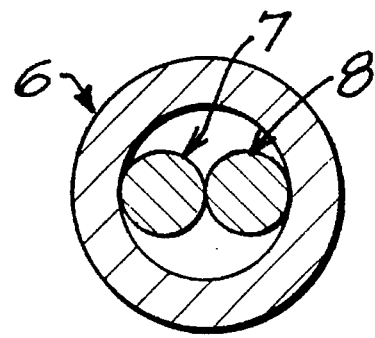
FIG. 4 is a cross-sectional view taken along line IV—IV in FIG. 3, drawn to a larger scale.

As shown in FIGS. 1, 2 and 4, a probe 1 according to the invention is held via its distal end in a chuck 2 of a coupling member 3 fitted with plugs 4 and 5 for connection to an IR source and an IR recorder device of a spectrometer. The probe 1 has an IR opaque sheath 6 holding a couple of IR transmitting optical fibers 7 and 8, one of which serves for light input, i.e. illumination, and the other for collecting the light output. Inside coupling device 3 the optical fibers 7 and 8 are split from each other with one being coupled to plug 4 and the other to plug 5.

On the proximal (relative to the sample) end of probe 1 there is mounted a detachable, sampling region-forming tubular sleeve 10 which has a terminal edge and an inner IR reflecting surface, e.g. a gold coating, and which is so dimensioned that the optical fibers 7 and 8 stop short of the terminal edge thus forming together with sleeve 10 a sampling cavity 11.

Figure 3:
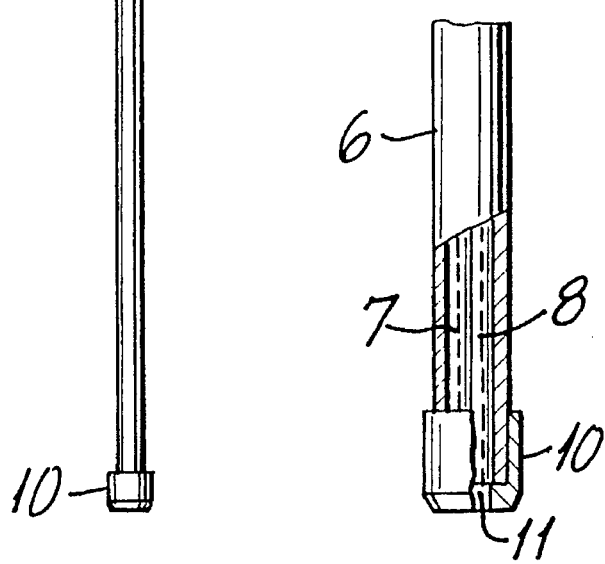
FIG. 3 is a partial axial section of another embodiment of a reflectance IR probe according to the invention.

The embodiment of the reflective probe according to the invention shown in FIG. 3 is essentially similar to that of FIGS. 1, 2 and 4 and accordingly corresponding parts are designated by the same numerals. The sole distinction between the two embodiments here shown is that in FIGS. 3 and 4 the sampling cavity 12 is formed with the proximal region of the sheath itself rather than being formed within a detachable tubular sleeve.

In operation the probe according to the invention is simply applied to the surface of a solid sample such as sample 17 in FIG. 3, or alternatively is immersed in a liquid sample. In case of a solid sample no surface preparation is required.

The IR opaque sheath 6 in the embodiments of the invention here described may, for example, be a metal tube typically having an inner diameter of 2.16 mm with the distance between the centers of the optical fibers 7 and 8 inside the sheath being about 1.08 mm and the depth of sampling cavity 11 in FIG. 2 and 12 in FIG. 3 also being about 1.08 min.

We claim:

1. A fiber optic reflectance probe for infrared spectroscopy of a sample, comprising a tubular sheath that is opaque to infrared radiation and having a longitudinal axis and a tubular sampling tip with a terminal edge transverse to said axis, said tubular sheath holding at least one light input optical fiber and at last one light output optical fiber, which input and output optical fibers terminate within said tubular sampling tip short of the terminal edge to form with the terminal edge a sampling cavity, an inner wall of said sampling cavity having an infrared radiation reflecting coating.

2. A fiber optic reflectance probe according to claim 1, wherein the sampling cavity is formed within an end portion of the sheath.

3. A fiber optic reflectance probe according to claim 1, wherein the sampling cavity is formed within a tubular sleeve detachably mounted on an end portion of the sheath.

4. A fiber optic reflectance probe according to claim 1, wherein the inner wall of the sampling cavity is gold coated.

* * * * *